(12) United States Patent
Freytag

(10) Patent No.: US 9,945,654 B2
(45) Date of Patent: Apr. 17, 2018

(54) PROBEHEAD OF AN NMR-MAS APPARATUS WITH A DEVICE FOR DETERMINING THE ANGLE BETWEEN THE MAS ROTOR AND THE STATIC MAGNETIC FIELD

(71) Applicant: Bruker BioSpin AG, Faellanden (CH)

(72) Inventor: Nicolas Freytag, Binz (CH)

(73) Assignee: Bruker BioSpin AG, Faellanden (CH)

( * ) Notice: Subject to any disclaimer, the term of this patent is extended or adjusted under 35 U.S.C. 154(b) by 0 days.

(21) Appl. No.: 15/441,991

(22) Filed: Feb. 24, 2017

(65) Prior Publication Data
US 2017/0248404 A1 Aug. 31, 2017

(30) Foreign Application Priority Data

Feb. 25, 2016 (DE) .................. 10 2016 202 943

(51) Int. Cl.
*G01V 3/00* (2006.01)
*G01B 7/30* (2006.01)
(Continued)

(52) U.S. Cl.
CPC .............. *G01B 7/30* (2013.01); *G01N 24/087* (2013.01); *G01R 33/07* (2013.01); *G01R 33/307* (2013.01); *G01R 33/38* (2013.01); *G01R 33/46* (2013.01)

(58) Field of Classification Search
CPC .................................................... G01R 33/307
(Continued)

(56) References Cited

U.S. PATENT DOCUMENTS

| 4,782,375 A | 11/1988 | Popovic |
| 5,760,586 A | 6/1998 | Foerster et al. |

(Continued)

FOREIGN PATENT DOCUMENTS

| JP | H3229183 A | 10/1991 |
| JP | 2011185867 A | 9/2011 |

OTHER PUBLICATIONS

Bodenhausen et al., "Optical Alignment in Magic-Angle NMR", Journal of Magnetic Resonance 48, Feb. 2, 1982, pp. 143-147.
(Continued)

*Primary Examiner* — Louis Arana
(74) *Attorney, Agent, or Firm* — Edell, Shapiro & Finnan, LLC

(57) ABSTRACT

A probehead of an NMR-MAS apparatus with a rotation axis (RA), which lies in an xz-plane, titled by an angle $\theta > 0$ relative to a z-axis. The angle $\theta$ is adjusted by tilting around a tilt axis (DA) parallel to the y-axis relative to a target angle $\theta_{target}$. An angle measurement apparatus (9) has a first sensor element (7), which, together with a second sensor element (8) generates sensor signals dependent on the amplitude B0 of the static magnetic field and the vectorial orientation between the magnetic field B0 and a sensitivity vector. Two sensitivity vectors have an angle $5° < \alpha i < 175°$ to the z-axis and an angle $\beta > 10°$ to each other. The angle between the rotation axis and the z-axis can be measured precisely and reliably over a large range, providing a feedback signal for regulated adjustment or tracking of the angle $\theta$.

20 Claims, 3 Drawing Sheets

(51) Int. Cl.
  *G01R 33/46* (2006.01)
  *G01R 33/38* (2006.01)
  *G01R 33/07* (2006.01)
  *G01N 24/08* (2006.01)
  *G01R 33/30* (2006.01)

(58) Field of Classification Search
  USPC .................................. 324/321, 320, 318
  See application file for complete search history.

(56) References Cited

U.S. PATENT DOCUMENTS

| | | |
|---|---|---|
| 8,203,339 B2 | 6/2012 | Johannessen et al. |
| 8,212,566 B2 * | 7/2012 | Mullen ............... G01R 33/307 |
| | | 324/207.13 |
| 8,547,099 B2 | 10/2013 | Takegoshi et al. |
| 2017/0146621 A1 * | 5/2017 | Freytag ............... G01R 33/307 |

OTHER PUBLICATIONS

Mihaliuk et al., "Optical Lever for Monitoring of the Magic Angle", Journal of Magnetic Resonance 223, 2012, pp. 46-50.
Office Action in corresponding German Application 102016202943.6, dated Nov. 3, 2016, along with English Translation.
Office Action in corresponding Japanese Application 2017031639, dated Sep. 26, 2017, along with English Translation.

* cited by examiner

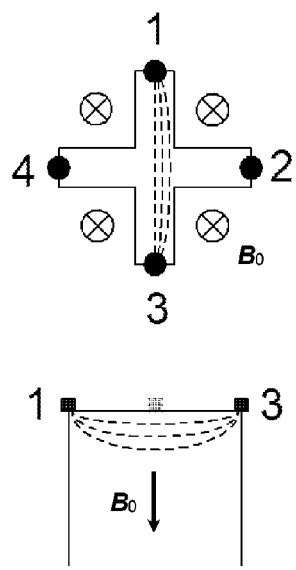
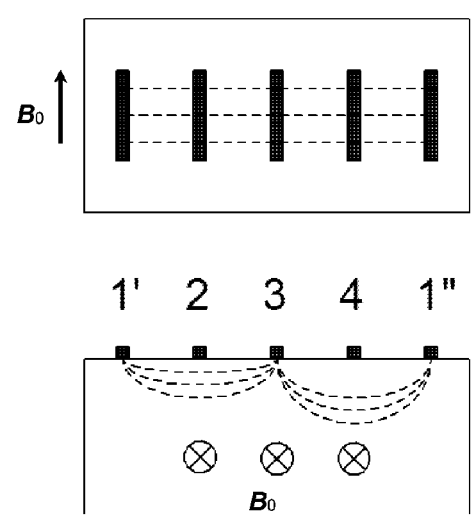
Fig. 2A  Fig. 2B
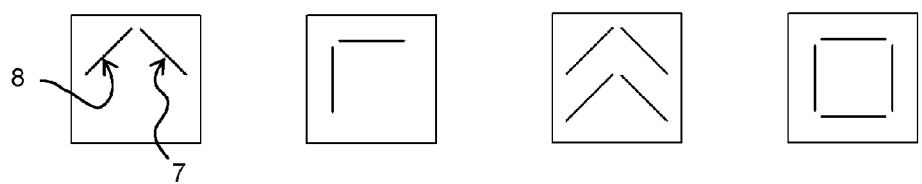
Fig. 3A  Fig. 3B

PRIOR ART

PROBEHEAD OF AN NMR-MAS APPARATUS WITH A DEVICE FOR DETERMINING THE ANGLE BETWEEN THE MAS ROTOR AND THE STATIC MAGNETIC FIELD

CROSS REFERENCE TO RELATED APPLICATIONS

This application claims foreign priority under 35 U.S.C. § 119(a)-(d) to German Application No. 10 2016 202 943.6 filed on Feb. 25, 2016, the entire contents of which are hereby incorporated by reference.

FIELD OF THE INVENTION

The invention relates to a probehead of a Nuclear Magnetic Resonance (NMR)-Magic Angle Spinning (MAS) apparatus, which is introduced in operation in a magnet system that generates a homogeneous, static magnetic field $B_0$ in a z-direction. In the operation of the NMR-MAS apparatus, the probehead includes an NMR measurement sample with a rotation axis that lies in a xz-plane and is tilted at an angle $\theta>0$ with respect to the z-axis. The angle $\theta$ can be adjusted by tilting around a tilt axis DA parallel to the y-axis around a target angle $\theta_{target}$. The origin of the coordinate (z=0) is defined as the intersection point of the rotation axis with the z-axis when the adjusted angle $\theta=\theta_{target}$. The probehead comprises an angle measurement apparatus with a first sensor element, which generates a signal $S(\theta)$ dependent on the angle $\theta$. One example of such an NMR-MAS probehead is known from U.S. Pat. No. 8,203,339 B2.

BACKGROUND

NMR spectroscopy is a method of instrumental analysis, with which in particular the chemical composition of measurement samples can be determined. Thereby, radio-frequency pulses are emitted into the measurement sample, which is located in a strong, homogeneous static magnetic field $B_0$, and the electromagnetic reaction of the sample is measured. With solid-state NMR spectroscopy, it is known to arrange the measurement sample at an angle that is tilted at the so-called "magic angle" of $\theta_m = \arccos(\sqrt{1/3}) \approx 54.74°$ with respect to the homogeneous, static magnetic field, in order to reduce line broadening due to anisotropic interactions. This measurement technique is usually described as "magic-angle spinning" (MAS). The angle $\theta_m$ is a solution of the second order Legendre polynomial $P_2(\cos(\theta_m))=0$, so that all interactions dependent on this Legendre polynomial disappear at this angle to the magnetic field. This is the case for three important interactions in solids: dipolar coupling, chemical shift anisotropy, and quadrupole interaction of the first order. As for polycrystalline measurement samples in which the crystal directions of individual crystallites are randomly oriented relative to the static field, the elimination of the interaction is achieved by a sufficiently fast rotation of the measurement sample at the magic angle. In this way, line broadening due to these interactions can be significantly reduced, ideally even to the natural line width.

NMR-MAS probeheads allow high resolution NMR spectroscopy to be carried out with solid, powder, or semi-solid (gel or paste) measurement samples. Thereby—as shown in FIG. 4—the measurement sample 5 is filled into a circular cylinder sample holder, the so-called rotor, which is rotated at very high speeds, with a rotation frequency in the range of a few kHz to over a hundred kHz, by means of compressed gases in a stator 10. The radial support is ensured by air bearings 20 in the stator, in the same manner as a holding force created by air flow holds the rotor in its axial position in the stator. The orientation of the rotation axis with respect to the static magnetic field is defined by the stator.

While for many NMR experiments in magnet systems with $B_0$ fields in the range from 7 T to 25 T, setting of the magic angle with a precision from 0.1° to 0.01° is sufficient, for some applications, such as, for example, satellite transition (ST-MAS) NMR or proton spectroscopy, a precision of up to 0.001° is required. The angle setting should remain constant over a wide temperature range and be maintained in a reproducible manner when changing the measurement samples. This places extremely high demands on the mechanical components, if the setting is to take place in a controlled instead of in a feedback-regulated manner. Consequently, a measurement apparatus that measures the angle between the rotation axis and the static magnetic field in a reliable manner would allow the angle to be maintained in a feedback-regulated manner.

In general, these probeheads are used in superconducting NMR magnet systems, in which the homogeneous, static magnetic field $B_0$ is oriented along a "bore hole," which specifies the z-axis of the laboratory coordinate system. Alternatively, magnet systems in which the static magnetic field is oriented orthogonal to a bore hole of the magnet, can also be used. This is the case, for example, with permanent magnets or some superconducting horizontal magnets.

FIG. 4 shows a cross-section of the measurement sample 5, the rotation axis RA and the direction of the static magnetic field. Also shown are the air bearings 20, the drive 30, the tilt axis DA, around which the stator 1 can be tilted in order to adjust the angle of the measurement sample 5 to the static magnetic field, and the air supply lines 6 for pressurizing the air bearings 20 and the drive 30. Further elements of the NMR probehead, such as radio frequency (RF) coils, walls, networks etc., are not shown for the sake of simplicity. The rotation axis RA of the measurement sample 5 is also referred to as z'-axis and has a joint origin with the z-axis. The z- and z'-axes lie in one plane, which is spanned by the x- and z-axes and the x'- and z'-axes. The y- and y'-axes of the two coordinate systems are identical.

In the prior art, MAS probeheads generally comprise an adjustment mechanism, which allows precise setting of the angle $\theta$ between the rotation axis RA of the measurement sample along the z'-axis and the static magnetic field $B_0$ along the z-axis. Such an adjustment mechanism that is integrated in the probehead is referred to as an "internal" or "integrated" mechanism. In general, the adjustment mechanism moves the measurement sample, the stator containing the bearing and the drive of the rotor, and the RF coils. This movement is induced by hoists, spindles and gear wheels, levers with linear movements or similar mechanisms, and primarily includes a rotation movement. However, generally rotation movements may also be combined with linear movements. Adjustment mechanisms with manual and motorized adjustment are known, particularly with electromotive adjustment. With many state-of-the-art probeheads, particularly those that are used in standard-bore magnet systems, i.e. magnet systems with a bore hole diameter of less than 60 mm, the angle adjustment can be carried out over a very large range, and also serves to facilitate removal of the measurement samples when changing samples. Probeheads that are tilted as a whole with respect to the magnet system to achieve the adjustment of the angle $\theta$, are also known.

Furthermore, U.S. Pat. No. 8,547,099 B2 describes an NMR system with a probehead without adjusting mechanism. With this NMR system, the tilt of the rotation axis (z'-axis) with respect to the probehead and the magnet system is kept constant, and the direction of the static magnetic field is tilted by generating a field $B_1$ with an additional electromagnetic coil. The additional electromagnetic coil is arranged around the measurement sample, so that the angle between the z'-axis and the direction of the linear combination of the $B_0$ and $B_1$ fields, correspond to the magic angle. Thus, with a probehead of such design, an electronic tilt of the angle θ is carried out.

Particularly when changing the sample temperature, removing or installing the probehead in the magnet system and changing measurement samples, the precision of the known adjustment mechanisms is often not sufficient for carrying out demanding NMR measurements. This particularly applies to proton spectroscopy and ST-MAS, where angle errors in the range of a few thousandths of a degree could lead to noticeable line broadenings in the measured spectra.

In the state of the art, the following method is used to adjust the angle θ between the rotation axis of the sample and the magnetic field direction: In general, a measurement sample (e.g. powdered potassium bromide) with the greatest possible dependency of the line width on the adjusted angle is measured via the NMR probehead. The line widths of the central line, and rotation side bands and/or the height of the lines and/or the ratio of amplitude/width between various lines are evaluated. Alternatively, an evaluation can be carried out directly on the time domain signal. Subsequently, the calibration measurement sample is removed and an actual measurement sample with the measurement substance is inserted in the probehead and measured using the angle setting from the calibration measurement.

In many cases this leads to errors, particularly if removing the probehead from the magnet system or tilting the stator to remove the rotor is required or a temperature change occurs between calibration and measurement.

MAS probeheads typically cover a very wide temperature range for the measurement samples. At the lower end of the temperature scale, there are probeheads that are designed for temperatures down to −50° C., −80° C., −130° C. or even for temperatures in the cryogenic area from 30K to 100K. In the upper temperature limit, values of temperatures up to +80° C., +150° C. or in the case of special samples even far beyond may be required. In most cases, the temperature of the measurement samples is ensured through use of a gas, whereby the air of the bearings and/or the drive air is also temperature-controlled to some extent.

Due to the compactness of the construction (the measurement sample diameters are typically in the range of 0.7 mm to 4 mm), the temperature of at least part of the tilt mechanism is close to the temperature of the measurement samples. Reproducing the adjustment of an angle with high precision and over a wide temperature range is technically extremely difficult to implement, and leads to high costs in the manufacturing of the mechanical parts.

Due to the complexity and difficulty of adjusting the angle θ of the rotation axis with respect to the z-axis in a precise and reproducible manner, there is a desire for a feedback-regulated adjustment, instead of the typical controlled adjustment using a calibration experiment but without feedback of the adjusted angle. In the prior art, three different concepts are known, which allow feedback between the adjusted angle and the measured angle:

U.S. Pat. No. 5,760,586 describes an MAS probehead, which includes automatic adjustment of the angle between the rotation axis of the measurement sample and the static field. One embodiment comprises a magnetic field sensor, in particular a Hall effect sensor for measuring said angle. Preferably, the Hall effect sensor is mounted in an inhomogeneous area of the static magnetic field and is moved by a mechanism within said area when the angle θ is adjusted in such a way that a calibration curve can correlate the adjusted angle θ with the measured magnetic field amplitude of the sensor.

U.S. Pat. No. 8,203,339 B2 describes an MAS probehead in which the adjustment of the angle between the rotation axis and the static magnetic field is regulated with a Hall effect sensor, whose orientation is as parallel as possible to the static field. The output signal (Hall voltage) is converted to an angle. Such a Hall sensor is shown in FIG. 4 with reference number 40.

The non-patent literature references titled "Optical alignment in magic-angle NMR" (G. Bodenhausen et al., J. Magn. Reson., 48 (1982), pp. 143-147) and "Optical lever for monitoring of the magic angle" (E. Mihaliuk, T. Gullion, J. Magn. Reson., 223, (2012), pp 46-50) describe a method of detecting the position of a laser beam reflected by the stator and using the detected position to determine the angle of the rotation axis with respect to the magnetic field.

The optical method is an indirect measurement of the angle. The signal does not directly depend on the magnetic field. Thus, it suffers from the disadvantage that the mechanical positioning of the probehead relative to the magnet field system affects the measured angle. Such a method is thus not suitable for delivering a measurement accuracy and reproducibility of 0.001°, particularly in the case where a probehead is removed.

The measurement of the angle using a Hall sensor is based on the Hall effect. This effect occurs for current-carrying conductors in a magnetic field and results in a voltage perpendicular to the current flow and field direction according to $$U_H = (A_H I/d) B_\perp$$

where $U_H$ is the Hall voltage, $A_H$ is the Hall coefficient, I is the control current, $B_\perp$ is the magnetic flux density orthogonal to the sensor plane, and d is the thickness of the conductor.

FIG. 2A shows a top-view drawing (top) and a cross-section (bottom) of a planar Hall sensor, whose plane is orthogonal to the magnetic field. The crosses in the top-view drawing symbolize the direction of the static magnetic field $B_0$. The Hall sensor has at least four contacts (1-4), whereby in FIG. 2A, a current flows between the contacts 1 and 3. The Hall voltage is established between the contacts 2 and 4 by the deviation of the electrons, whose paths are symbolized by dashed lines.

Unfortunately, in reality the Hall effect is less ideal than suggested by this formula.

The Hall coefficient $A_H$ depends on the temperature-dependent charge carrier density (electrons/holes) and the mobility of said charge carriers. This results in a marked temperature dependence of the Hall voltage. Additionally, with real sensors, a voltage caused by a combination of a temperature-related mechanical stress and a piezo-electric effect further distorts the temperature dependence of the Hall voltage.

In addition to the temperature dependence, effects depending on the magnetic field also occur. For example, the band structure of conductors generally changes in the magnetic field, which leads to non-linearities of the Hall effect, especially in strong magnetic fields.

Furthermore, Hall sensors generally experience an offset voltage in the zero field value, which occurs, for example, due to minor asymmetries of the contacts and/or positioning of the sensor with respect to the crystal axis of the substrate used. Furthermore, the Hall sensors may experience symptoms of aging, leading to long-term drifts. Thermoelectric voltages in the supply lines and contacts also lead to temperature-dependent errors due to an inadequate measurement assembly.

Moreover, additional magnetoresistive effects, such as the planar Hall effect (PHE), can be problematic for angle detection. With the planar Hall effect a voltage $$U_{PHE}(A_{PHE}I/d)B_i^2 \sin(2\varphi)$$

occurs, where $\varphi$ is the angle between the projection of the magnetic field in the sensor plane and the control current. Additionally, $A_{PHE}$ is only constant as a first approximation.

If a Hall sensor is exposed to a magnetic field that is not orthogonal to the sensor plane, then the output signal is the total of the Hall voltage and the planar Hall voltage.

$$U=(A_H I/d)B_\perp + (A_{PHE}I/d)B_i^2 \sin(2\varphi)$$

Furthermore, spin-dependent scattering processes can occur (abnormal Hall effect) during operation at cryogenic temperatures, as well as Shubnikov-de Haas and Quantum-Hall effects.

Thus, precision measurements require careful calibration over the entire application range (magnetic field strength, angle and temperature), which has to be repeated at regular intervals to correct aging effects. In addition, it is desirable to use only sensors in which the offset voltages are already reduced as far as possible due to the design and "perturbations" such as the PHE are kept to a minimum. For example, the PHE of a Hall sensor based on a heterojunction is up to 50 times smaller than the PHE of a comparable Hall sensor from a single, continuously doped semiconductor.

The methods known from the prior art for determining and adjusting the magic angle of NMR probeheads using a magnetic field measurement are based on two different principles: In U.S. Pat. No. 8,203,339 B2, a Hall sensor is mounted in the static magnetic field in such a way that the sensor plane and thus the orientation of the sensitivity vector is as parallel as possible, i.e. at an angle below 5°, to said sensor. The obtained Hall voltage is then converted into an angle and used for adjusting the angle.

This approach has several problems:
1. If the sensor is in a parallel orientation to the field, it is operated in a range in which the PHE can lead to comparable or even higher voltages than the normal Hall effect. The angle measurement is thus no longer primarily dependent on the orthogonal component of the magnet field, but on the angle of the current to the parallel component of the field.
2. The adjustment of the angle depends directly on the accuracy of the measurement of the Hall voltage and measurement current.
3. Any drift and changed Hall coefficients (temperature dependence) result in angle errors, unless the angle of the sensor is adjusted to exactly 0°.

U.S. Pat. No. 5,760,586 also uses a Hall sensor as a magnetic field sensor. However, the hall sensor is positioned in an inhomogeneous area of the magnetic field. A rotation movement of the stator defining the rotation axis of the measurement sample is turned into a translation of the sensor in the inhomogeneous field via a mechanism. The obtained Hall voltage is then converted into an angle via a calibration table and used for adjusting said angle.

This approach poses the following problems:
1. A position inaccuracy along the z-axis results in angle errors. This inaccuracy can occur, for example, if the probehead position is referenced with respect to a shim system, but said shim system changes its length relative to the fixing point at the magnet due to temperature variations.
2. The inhomogeneous field depends on the adjusted currents of the shim system. Fluctuations of the shim fields due to the fluctuations of the shim current sources are also transferred directly to fluctuations of the measured angle.
3. The adjustment of the angle depends directly on the accuracy of the measurement of the Hall voltage and measurement current.
4. Any drift and changed Hall coefficients (temperature dependence) result in angle errors.

SUMMARY

Objects of the invention include providing an NMR-MAS probehead, of the type defined above, which makes it possible to measure the angle $\theta$ between the rotation axis and the z-axis over the largest possible range, with high precision and reproducibility, in a cost-effective manner and with simple means which are readily available, by producing a feedback signal, which in turn permits a feedback-regulated adjustment of the angle $\theta$.

BRIEF DESCRIPTION OF THE DRAWINGS

Embodiments of the invention are illustrated in the drawing, and are explained in more detail with reference to the drawings, in which:

FIG. 2A shows a top-view and a cross-sectional view of a planar Hall sensor with four contacts;

FIG. 2B shows a top-view and a cross-sectional view of a vertical Hall sensor with five contacts;

FIG. 3A shows positioning options for the first and second sensor element;

FIG. 3B shows positioning options for groups of sensor elements; and

DETAILED DESCRIPTION

Figure 1:
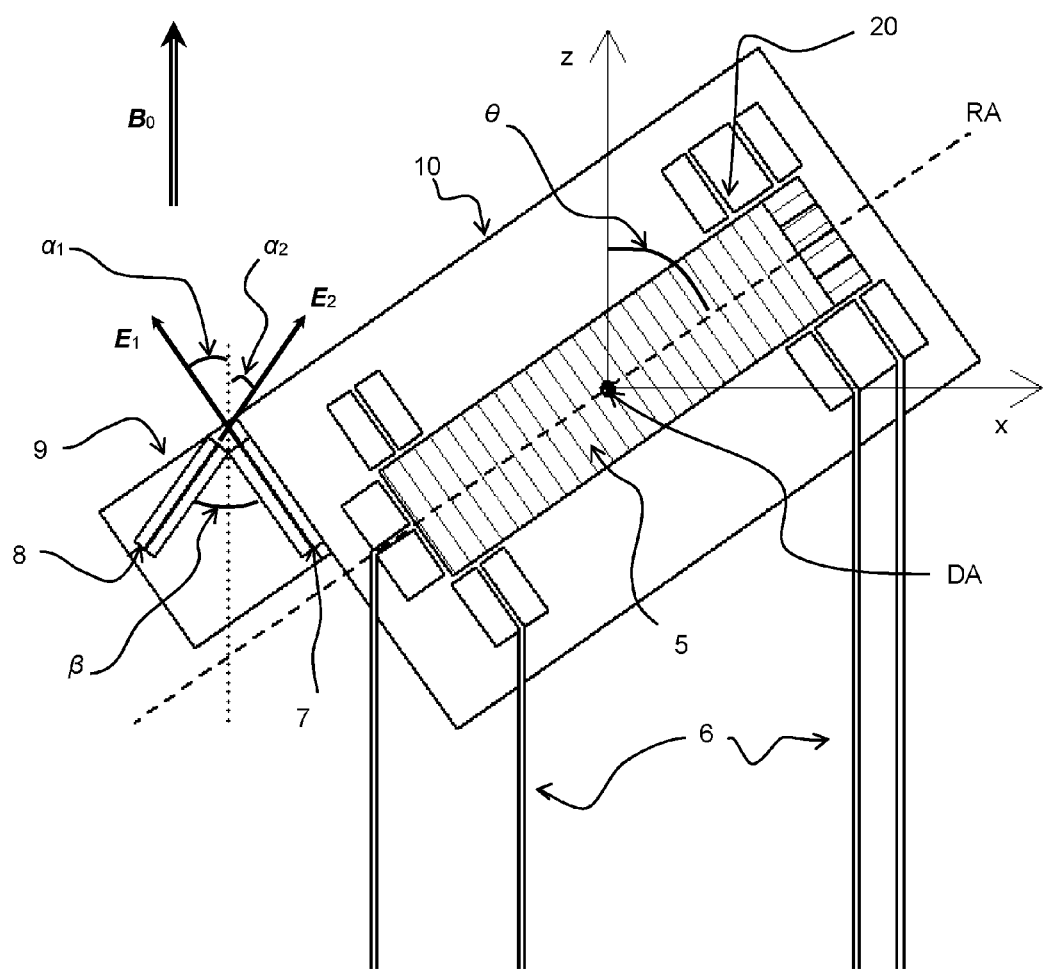
FIG. 1 is a diagrammatic cross-sectional view of an inventive NMR probehead with two angle measurement sensors.
Figure 4:
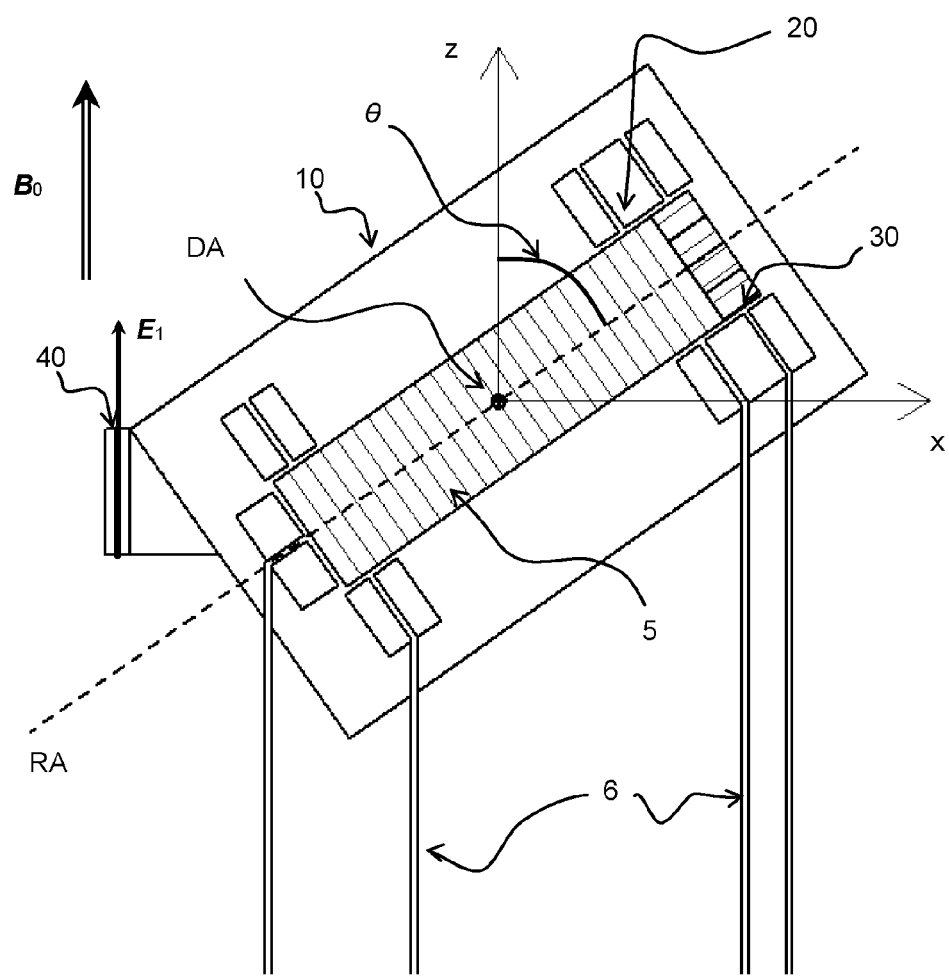
FIG. 4 is a schematic cross-sectional view of a conventional NMR probehead with a Hall sensor mounted parallel to the static field for determining the angle of the rotation axis relative to the static magnetic field.

The error susceptibility in adjusting the magic angle of MAS probeheads due to inadequacies of the measurement elements can be solved in a surprisingly simple and effective way, using readily available technical means. The angle measurement apparatus comprises a plurality of sensor elements, which each generate a sensor signal $T_i$ ($E_i$, $B_0$) 0) that depends on the amplitude $B_0$ of the static magnetic field $B_0$ and the angular orientation between the magnetic field $B_0$ and at least one sensitivity vector $E_i$. The sensitivity vectors $E_i$ are oriented such that they are orthogonal to the magnetic field $B_0$ at the highest possible signal $T_i^{max}$. The signal $S(\theta)$ depends on the angle $\theta$, and is a function $f(T_i)$ of the plurality of sensor signals $T_i(E_i, B_0)$ At least two sensitivity vectors $E_i$ have an angle $\alpha_i$ with respect to the z-axis and the angles $\alpha_i$ are $5° < \alpha_i < 175°$. Additionally, at least two of the sensitivity vectors $E_i$ have an angle $\beta$ to each other for which $\beta > 10°$.

The probehead according to the invention thus comprises a plurality of magnetic field measurement elements, of which at least two have an angle greater than 5° with respect to the static field and an angle of more than 10° with respect to each other. A combined signal of the measured sensor signals is used for determining the angle of the probehead with respect to the static magnetic field.

Initially, the previously known technique, which is now improved by the invention, will be described for ease of understanding the improvement:

As already described above, the precise adjustment of the angle θ between the rotation axis of a measurement sample and the direction of the static magnetic field $B_0$ in an MAS probehead without a regulated feedback loop is not possible, or is possible only at very high costs for precision mechanics and calibration. Probeheads containing a sensor for measurement of said angle are known. One of the most promising solutions is a Hall sensor whose sensor plane is mounted in the homogeneous area in an orientation as parallel as possible to the static magnetic field. However, these probeheads do not allow long-term operation without recalibration, particularly with varying the temperature of the measurement samples.

Sensors, which can be used for measuring the angle with respect to the static magnetic field of a magnet can be characterized by a sensitivity vector E. Subsequently, these sensors generate a signal $T(E, B_0)$, which depends on the amplitude $B_0$ of the static magnetic field and the angular orientation between the magnet field $B_0$ and a sensitivity vector E. The sensitivity vector E is defined such that the sensor generates the highest possible signal $T^{max}$ when the vector E is orthogonal to the magnetic field $B_0$.

For a planar Hall sensor, whose signal $T \sim U_H = (A_H I/d) B_\perp$ is maximized for $B_\perp = B_0$, the sensitivity vector is thus orthogonal to the direction of the surface normal of the sensor plane and in the plane spanned by the magnetic field and the surface normal.

Therefore, the highest sensitivity of the measurement signal $T(E, B_0)$ to an angle change, i.e. the derivation of the measurement signal against the angle between E and $B_0$, is achieved when a Hall sensor is mounted in an orientation that is as parallel as possible to the static magnetic field.

For a sensor based on the PHE, however, the signal is $T \sim U_{PHE} = (A_{PHE} I/d) B_i^2 \sin(2\varphi)$. In this case there are two solutions that lead to $T^{max}$. For the purposes of the invention, any solution among the possible equivalent solutions may be selected for defining the sensitivity vector. Within the scope of the invention, the definition of the sensitivity vector may also be defined independently from the control. For example, when using lock-in detection for a Hall sensor, there are two equivalent solutions with opposite vector directions, one of which is selected as the sensitivity vector.

A major disadvantage of Hall sensors is their usually high offset voltage, i.e. an output signal which also occurs at zero magnetic field. A very efficient method known from the prior art to eliminate or reduce such offset voltages is the so-called spinning-current detection, where the control current and voltage electrodes of the Hall sensor are periodically exchanged. The spinning-current method comprises continuously tilting the measurement device at a Hall sensor with at least N contacts at a clock frequency, typically in the kHz range. The measurement device is cyclically tilted by an angle of $\varphi = 360°/N$ and all of the measurement signals add up to a measurement of a full rotation by 360°. With a lateral Hall sensor with four electrodes, of which two electrodes are located opposite each other, each electrode is used alternately as a control electrode or measurement electrode. At each change of the spinning current phase, each electrode alternates between being used as a control current electrode and being used as a measurement electrode for determining the Hall voltage. In one phase or one cycle, the control current flows from a first electrode to the opposite electrode, whereby the Hall voltage is picked up at the orthogonally positioned electrodes. In the next cycle, the measurement direction is tilted by 90°, so that the electrodes, which were used for measuring the Hall voltage in the previous cycle, serve for current injection. By summing over all four cycles or phases, the offset voltages substantially cancel each other, so that only the portions of the signal that actually depend on the magnetic field remain. A requirement for this, however, is that the arrangement of the contact electrodes is as symmetrical as possible.

Thereby, a linear component of the offset can be suppressed by a 2-phase method. A 4-phase method can also eliminate squared terms and thermoelectric effects. Even higher orders result in further reductions of offset voltages. Another advantage of the spinning-current detection is the reduction of the $1/f$ noise.

U.S. Pat. No. 4,782,375 describes sensors that are sensitive to magnetic field components in the two spatial directions orthogonal to the substrate surface normal. Solutions for the realization of these so-called vertical Hall sensors are known, which allow the use of standard semiconductor technologies for their manufacture. With such vertical Hall sensors that are obtained by conformal mapping from known geometries of lateral Hall sensors, an electrically conductive area extends vertically to the surface of a substrate into said substrate. All connection areas along one side of the electrically conductive area are situated on the surface of the substrate. FIG. 2B schematically shows the structure of said vertical Hall sensor, whereby, similar to the planar Hall sensor, a top-view drawing (top) and a cross-section (bottom) are shown. Here again, the crosses in the cross-sectionals view symbolize the direction of the static magnetic field $B_0$.

The Hall sensor has at least five contacts (1', 1", 2-4), whereby in the FIG. 2B, a current flows between the contacts 1' and 3 and between 1" and 3. The Hall voltage is established between the contacts 2 and 4 by the deviation of the electrons in the magnetic field, whose paths are symbolized by dashed lines.

Vertical Hall sensors have the great advantage that multiple sensors can be produced at any angle relative to each other. The multiple sensors can be manufactured on the same semiconductor substrate in a single process step. As a result, these sensors are very similar to each other, for example, in terms of the charge carrier density. The sensors also show very similar behaviors with respect to temperature variations, aging, stress, etc. If a substrate is manufactured from a material with good heat conducting properties, such as silicon, the small distances between two vertical Hall sensors ensure that both sensors have identical temperatures and thus temperature-dependent effects have a substantially identical impact on both sensor elements.

FIG. 3A shows four possible implementations of vertical Hall sensors on a substrate. Here, the substrate has a fixed orientation with respect to the crystal direction and merely the positioning of the vertical Hall sensors, symbolized by lines, is changed. The two upper variants have two sensors each, which are at an angle of 90° to each other. Depending on the orientation of the substrate lattice, one of the variants can be of such a design that both sensors are equivalent thus having almost identical characteristics. The bottom row shows sensors at an arbitrary angle and orientation to the substrate.

According to the invention, in the prior art, the problems of the MAS probeheads with angle sensors are solved by designing the MAS probehead such that, instead of the previous single sensor, it comprises at least two sensors 7,8, which are positioned at an angle>5° to the z-axis and at an angle>10° to each other A signal combined from the signals of the at least two sensors is used for determining the angle.

For example, if two Hall sensors are mounted in such a way that their sensitivity vectors each have an angle of $\alpha_{1,2}=45°$ to the z-axis and an angle of $\beta=90°$ to each other with the adjusted angle $\theta=\theta_{target}$, then, for a substantially identical control current and substantially identical Hall sensors, a substantially identical output amplitude of the individual sensors is to be expected:

$$U_H^i = (A_H^i(T^i)I^i/d^i)B_\perp \text{ with } B_\perp = B_0 \sin 45° = B_0\sqrt{2}/2,$$

i.e. $U_H^1 \approx U_H^2$ if $A_H^1(T) \approx A_H^2(T)$ and $T^1 \approx T^2$ and $I^1 \approx I^2$ If the conduction in the Hall sensor is based on electrons and holes, then the Hall coefficient is $$A_H = \frac{n_e\mu_e^2 - n_p\mu_p^2}{e(n_e\mu_e + n_p\mu_p)^2}.$$

Since the mobility of electrons in intrinsic semiconductors is generally much higher than the mobility of holes this is simplified to $$A_H \approx \frac{1}{e\,n_e}.$$

The charge carrier density n(T) depends on the temperature. In non-degenerate semiconductors with a bandgap $\Delta E \gg k_B T$, the Fermi distribution required in the metal for describing the electrons can be replaced by the Boltzmann distribution, and we obtain $$n(T) \sim T^{2/3} e^{-\Delta E/2k_BT} \approx T^{2/3}(1-\Delta E/(2k_BT))$$

If now, instead of a single sensor signal, the ratio between two sensor signals is measured, with both sensors having the same temperature T and being manufactured from the same semiconductor material, the resulting signals S(T) behaves like $$S(T) \sim \frac{A_H^1(T)}{A_H^2(T)} = \frac{n_e^2(T)}{n_e^1(T)} \sim \frac{T^{2/3}e^{-\Delta E/2k_BT}}{T^{2/3}e^{-\Delta E/2k_BT}} = const$$

Thus, the use of a signal S as a control parameter generated from the ratio of two measurement elements enables the elimination of the temperature dependence of the charge carrier density and thus the Hall effect without calibration. As the aging of a sensor also primarily affects the charge carrier density, a combined measurement element of such design has long-term stability and does not change its output signal over time. If the control current of both sensors is generated from a single current source, another advantage of the method is that by calculating the ratio, any noise in the control current is also eliminated. Thus, ultra-precise current regulation is not required for accurate determination of the angle.

Such an MAS probehead is shown schematically in FIG. 1. In addition to showing the measurement sample 5, the rotation axis RA and the direction of the static magnetic field, FIG. 1 also shows the air bearings 20, the drive 30, the tilt axis DA around which the stator can be tilted in order to adjust the angle of the measurement sample to the static magnetic field, and the air supply lines 6 for pressurizing the air bearings and the drive. Further elements of the NMR probehead, such as RF coils, walls, networks etc., are not shown for the sake of simplicity.

In this embodiment, two sensors 7 and 8 are shown. In this specific embodiment, sensor 7 is mounted orthogonally to the rotation axis. The two sensors and thus also their sensitivity vectors have the same absolute value of the angle with respect to the static magnetic field.

Moreover, when using different angles $\alpha_1 \neq \alpha_2$ of the sensitivity vectors of the two sensors with respect to the magnetic field $B_0$ or the z-axis, in combination with different control currents $I^1 \neq I^2$, there is the possibility of using different sensors, at least over a certain range, substantially in parallel. In other words, the two sensors will have substantially identical signals $T^i(\theta)$, so that precise measurement of the angle is possible at least within a certain angle adjustment range for the angle θ. If the control currents are formed from a single control current by attenuation, then only the noise of the attenuation element contributes to the noise of the output signal, but not the noise of the original control current.

In a different example, the PHE is identified as a major portion of the deviation of the measurement sensor from an ideal measurement sensor, the following applies to each sensor:

$$U^i = (A_H^i I/d)B_\perp + (A_{PHE}^i I/d)B_\perp^2 \sin(2\varphi).$$

With a skillful arrangement of the sensors, the combined signal of the two sensors can be set such that $(\varphi)=0$. In other words, the offset voltage generated by the planar Hall effect can be eliminated by the addition/subtraction of two voltages. The addition/subtraction of two signals can also contribute to the elimination of other additive interferences.

If more than two sensor elements are used, multiple parameters can be eliminated by a combination of addition/subtraction and division of the sensor element signals. This allows a long-term, stable measurement, which is substantially independent from external parameters, for determining the angle θ in an MAS probehead.

FIG. 3B shows four possible implementations of four vertical Hall sensors on a substrate. Here, the substrate has a fixed orientation with respect to the crystal direction and merely the positioning of the vertical Hall sensors, symbolized by lines, is changed. The two upper variants have two sets of two identically oriented sensors each, which are at an angle of 90° to each other. The bottom row shows four sensors at different or pairwise different angles and orientations to the substrate.

In some embodiments of the probehead according to the invention, the angles $\alpha_i$ are: $30° < \alpha_i < 60°$ Vi, preferably $\alpha_i \approx 45°$. Preferably, two sensors are mounted at 45° to the static magnetic field. This results in an angle of 90° with respect to each other. If identical measurement elements with $|\alpha_i|=|\alpha_j|$ are used, the output signal of both sensors is the same for this positioning and the measurement sensitivity of both sensors is identical.

In other embodiments, the two sensors are mounted at an angle<45°, or better at an angle<20°, or even better at an angle<10°, and ideally at an angle≤5° with respect to the static magnetic field. In this way, the sensitivity of both sensors to angle changes is maximized. However, to be able to achieve a high precision of the measurement, a very good compensation of the offset voltages must be provided in this case.

Other embodiments of the inventive probehead are provided in a device for automated adjustment of the angle θ based on the i sensor signals $T_i(E_i, B_0)$. This allows, particularly in conjunction with robots for changing measurement samples, fully automated operation of the NMR spectrometer, even in the absence of a user, and thus a higher utilization of the spectrometer hardware. Thereby, the cost of this analytical method can be reduced for users.

Other advantageous embodiments of the invention are characterized in that at least two groups of at least two sensors are interconnected in such a way that the total of the ratios of the measurement signals or the ratio of the totals of the sensors within each group of the at least two groups is obtained as a feedback-regulating signal for adjusting or tracking the angle θ. By summing and calculating of the ratio of measurement signals, additive as well as multiplicative dependencies of the measurement signal on external parameters can be eliminated. Thereby, a temperature-independent signal that is stable long-term can be made available for feedback-regulated adjustment or tracking of the magic angle and high-precision angle adjustment can be enabled. Tracking of the angle allows a more cost-effective design of mechanical components and enables long-term consistency of the angle adjustment by means of feedback-regulated compensation mechanisms. This allows long-term measurements in a cost-efficient manner.

In another embodiment, the plurality of measurement elements are manufactured on a shared substrate or carrier—generally at the same time. This results in temperature dependencies and aging behaviors that are as identical as possible. Thereby, the error tolerance of the measurement method can be increased.

This is particularly advantageous when using Hall sensors of the vertical Hall sensor type, as the plurality of sensors can be manufactured in a single process step on a single substrate, having comparable characteristics. Moreover, as long as the substrate has a high thermal conductivity, the temperature of the two sensors can be assumed to be identical. Therefore, in some embodiments of the invention, at least some of the sensor elements, preferably all sensor elements, comprise Hall sensors. These sensors are particularly advantageous for strong magnetic fields and precision measurements. When other types of magnetic field sensors are used, sensors from the same production batch, ideally sensors also manufactured on the same substrate, should be installed. This ensures the long-term stability of the combined signal. When physically separated sensors are used, a tight thermal coupling during assembly ensures identical temperatures in all of the sensors.

In one embodiment with Hall sensors, an Alternating Current (AC) or lock-in measurement is carried out. This assists in compensating for offset voltages.

In another embodiment with Hall sensors, the Hall sensors are read by means of the spinning-current method. The Hall sensors are read using at least a 2 phase measurement (double orthogonal switching), but preferably 4 or 8 phase spinning-current measurements are used. This efficiently suppresses various offset voltages and the noise is minimized.

In another embodiment, the plurality of sensors are attached to the stator, which is manufactured from a material with a high thermal conductivity $\lambda_S$. The sensors are attached to the stator by means of a connection with a high thermal conductivity. The high thermal conductivity ensures that the measured angle quickly displays the correct value, even while changing measurement sample temperature. It also ensures that no slow drifts occur due to thermal effects in the supports. Since the stator defines the direction of the rotation axis RA via the radial supports 20 of the rotor, in which the measurement sample 5 is located, temperature gradients are minimized in the angle impacts on the regulating signal S.

In one example, the thermal conductivity $\lambda_S$ is greater than 30 W/(m K), or preferably $\lambda_S$ is less than 100 W/(m K), Ideally, $\lambda_S$ is less than 200 W/(m K)

In another embodiment, magnetodiodes or magnetotransistors are used as sensor elements. These sensors are particularly cost-effective to manufacture and integrate in measurement electronics.

In further embodiments of the invention, three or more sensor elements are available, i.e. i≥3, and the sensor elements preferably have an identical design. In these embodiments, the sensitivity vectors $E_i$ of the sensors can be partially identical. By using a larger number of sensors, for example, the cancellation of the noise and the offset voltage can be improved by means of averaging.

In one embodiment, a plurality of sensor elements each with the same sensitivity vector $E_i$ are mounted orthogonally. The orthogonal coupling of these two sensors can generally reduce offset effects and PHE by at least one order of magnitude.

An NMR spectrometer also falls in the scope of the present invention. The NMR spectrometer includes a magnet system, which can generate a homogeneous static magnetic field $B_0$ in a z-direction. The NMR apparatus also includes an apparatus for carrying out NMR-MAS measurements comprising a rotatable mechanism with a stator carrying a movable rotor, in which an NMR measurement sample can be filled. The NMR spectrometer further includes a probehead of the inventive type described above.

In a process variant for operation of this NMR spectrometer, the ratio of the signals $T_i (E_i, B_0)$ of two sensors is used as a feedback-regulating signal for adjusting or tracking the angle θ. The ratio of the currents through the two sensors, the design of the sensors, and/or the angles of the sensors with respect to the z-axis are adjusted in such a way that the measurement signal is as close to 1 as possible for $\theta=\theta_{target}$. This design of a probehead allows for the compensation of multiplicative effects in the signal measurement of the sensors used.

In another process variant, the difference of the signals $T_i(E_i, B_0)$ of two sensors is used as a feedback-regulating signal for adjusting or tracking the angle θ. The ratio of the currents through the two sensors, the design of the sensors, and/or the angles of the sensors with respect to the z-axis are adjusted in such a way that the measurement signal is as close to 1 as possible for $\theta=\theta_{target}$. This design lowers the sensitivity of the measurement to variations of the sensor signals due to extreme conditions having an additive effect to the sensor signal as much as possible.

In another process variant, at least two groups of at least two sensors are interconnected in such a way that the total of the ratios or the ratio of the total of the measurement signals of the sensors within each group of the at least two groups serves as a measurement signal. This eliminates additive as well as multiplicative dependencies of the measurement signal on external parameters.

Also advantageous is a process variant for operation of the NMR spectrometer, in which at least some of the sensor elements in the probehead are Hall sensors that are used to carry out an AC or lock-in measurement The Hall sensors may be read by means of the spinning-current method.

Further advantages of the invention will become apparent from the description and the drawings. Also, the above-mentioned and further detailed features according to the invention can be used individually or collectively in any combination with each other, respectively. The embodiments shown and described should not be seen as an exhaustive list, but are rather an example of the description of the invention.

LIST OF REFERENCE SIGNS AND NAMES

(10) stator
(20) air bearings
(30) turbine/rotor drive
(40) Hall sensor
(5) measurement sample
(6) air lines
(7) first sensor element
(8) second sensor element
(9) angle measurement apparatus
(RA) rotation axis
(DA) tilt axis

What is claimed is:

1. A probehead of a Nuclear Magnetic Resonance (NMR)-Magic Angle Spinning (MAS) apparatus, which is introduced in operation in a magnet system that generates a homogeneous static magnetic field $B_0$ along a z-axis, the probehead comprising:
   a measurement sample with a rotation axis that lies in an xz-plane and is tilted at an angle $\theta>0$ with respect to the z-axis, wherein the angle $\theta$ is configured to adjust by tilting the rotation axis around a tilt axis parallel to a y-axis to reach a tilt at which the angle $\theta$ equals a target angle $\theta_{target}$, and wherein z=0 is defined as a point of intersection of the rotation axis and the z-axis at the angle $\theta=\theta_{target}$; and
   an angle measurement apparatus that generates a signal $S(\theta)$ dependent on the angle $\theta$, the angle measurement apparatus comprising a plurality of sensor elements
wherein each sensor element of the plurality of sensor elements generates a sensor signal that depends on the amplitude of the homogenous static magnetic field $B_0$ and the angular orientation between the homogenous static magnetic field $B_0$ and a respective sensitivity vector associated with the sensor element, wherein each sensor element generates a maximum sensor signal when the respective sensitivity vector is oriented orthogonal to the homogenous static magnetic field $B_0$, and wherein the signal $S(\theta)$ is a function of at least two sensor signals from at least two sensor elements associated with at least two respective sensitivity vectors, each of the at least two respective sensitivity vectors being oriented at an angle $\alpha_i$ between 5° and 175° with respect to the z-axis, and wherein the at least two respective sensitivity vectors are oriented at an angle $\beta>10°$ with respect to each other.

2. The probehead according to claim 1, wherein each of the at least two respective sensitivity vectors are oriented at the angles $\alpha_i$ between 30° and 60°.

3. The probehead according to claim 2, wherein each of the at least two respective sensitivity vectors are oriented at the angles $\alpha_i=45°$.

4. The probehead according to claim 1, wherein each of the plurality of sensor elements is mounted at an angle<45° with respect to the homogenous static magnetic field $B_0$.

5. The probehead according to claim 4, wherein each of the plurality of sensor elements is mounted at an angle<20° with respect to the homogenous static magnetic field $B_0$.

6. The probehead according to claim 5, wherein each of the plurality of sensor elements is mounted at an angle<10° with respect to the homogenous static magnetic field $B_0$.

7. The probehead according to claim 6, wherein each of the plurality of sensor elements is mounted at an angle<5° with respect to the homogenous static magnetic field $B_0$.

8. The probehead according to claim 1, further comprising an automated angle adjustment device for adjusting the angle $\theta$ based on the sensor signals.

9. The probehead according to claim 1, wherein the plurality of sensor elements comprises at least two groups of at least two sensor elements that are interconnected such that a total of ratios of the sensor signals within each group of the at least two groups provides a regulating signal that adjusts or tracks the angle $\theta$.

10. The probehead according to claim 1, wherein the plurality of sensor elements are manufactured on a shared substrate or carrier.

11. The probehead according to claim 1, further comprising a stator that is manufactured from a material with a first thermal conductivity $\lambda_1$, wherein the plurality of sensor elements are attached to the stator through a connection with a second thermal conductivity $\lambda_2$, and wherein the first thermal conductivity $\lambda_1$ and the second thermal conductivity $\lambda_2$ are each greater than 30 W/(m K).

12. The probehead according to claim 11, wherein the first thermal conductivity $\lambda_1$ and the second thermal conductivity $\lambda_2$ are each greater than 100 W/(m K).

13. The probehead according to claim 12, wherein the first thermal conductivity $\lambda_1$ and the second thermal conductivity $\lambda_2$ are each greater than 200 W/(m K).

14. The probehead according to claim 1, wherein at least some of the plurality of sensor elements comprise Hall sensors.

15. The probehead according to claim 14, wherein all of the plurality of sensor elements comprise Hall sensors.

16. The probehead according to claim 1, wherein at least some of the plurality of sensor elements comprise magnetodiodes or magnetotransistors.

17. The probehead according to claim 16, wherein all of the plurality of sensor elements comprise magnetodiodes or magnetotransistors.

18. The probehead according to claim 1, wherein the plurality of sensor elements includes at least three sensor elements that have an identical design and have at least partly identical sensitivity vectors.

19. The probehead according to claim 1, wherein at least two particular sensor elements of the plurality of sensor elements have a common sensitivity vector, and the at least two particular sensor elements are coupled orthogonally.

20. A Nuclear Magnetic Resonance (NMR) spectrometer comprising:
   a magnet system configured to generate a homogeneous static magnetic field $B_0$ along a z-axis;
   an NMR Magic Angle Spinning (MAS) apparatus for carrying out NMR-MAS measurements, the NMR-MAS apparatus comprising:

a rotatable mechanism with a stator carrying a movable rotor configured to support an NMR measurement sample; and a probehead, which is introduced in operation in the magnet system and comprises:

a measurement sample with a rotation axis that lies in an xz-plane and is tilted at an angle $\theta>0$ with respect to the z-axis, wherein the angle $\theta$ is configured to adjust by tilting the rotation axis around a tilt axis parallel to a y-axis to reach a tilt at which the angle $\theta$ equals a target angle $\theta_{target}$, and wherein z=0 is defined as a point of intersection of the rotation axis and the z-axis at the angle $\theta=\theta_{target}$; and an angle measurement apparatus that generates a signal $S(\theta)$ dependent on the angle $\theta$, the angle measurement apparatus comprising a plurality of sensor elements wherein each sensor element of the plurality of sensor elements generates a sensor signal that depends on the amplitude of the homogenous static magnetic field $B_0$ and the angular orientation between the homogenous static magnetic field $B_0$ and a respective sensitivity vector associated with the sensor element, wherein each sensor element generates a maximum sensor signal when the respective sensitivity vector is oriented orthogonal to the homogenous static magnetic field $B_0$, and wherein the signal $S(\theta)$ is a function of at least two sensor signals from at least two sensor elements associated with at least two respective sensitivity vectors, each of the at least two respective sensitivity vectors being oriented at an angle $\alpha_i$ between 5° and 175° with respect to the z-axis, and wherein the at least two respective sensitivity vectors are oriented at an angle $\beta>10°$ with respect to each other.

* * * * *